(12) United States Patent
Martins

(10) Patent No.: US 10,953,072 B2
(45) Date of Patent: *Mar. 23, 2021

(54) TREATMENT OF HEPATITIS DELTA VIRUS INFECTION WITH INTERFERON LAMBDA

(71) Applicant: Eiger BioPharmaceuticals, Inc., Palo Alto, CA (US)

(72) Inventor: Eduardo Bruno Martins, Palo Alto, CA (US)

(73) Assignee: EIGER BIOPHARMACEUTICALS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/999,239

(22) PCT Filed: Feb. 17, 2017

(86) PCT No.: PCT/US2017/018466
§ 371 (c)(1),
(2) Date: Aug. 17, 2018

(87) PCT Pub. No.: WO2017/143253
PCT Pub. Date: Aug. 24, 2017

(65) Prior Publication Data
US 2019/0111110 A1    Apr. 18, 2019

Related U.S. Application Data

(60) Provisional application No. 62/297,759, filed on Feb. 19, 2016.

(51) Int. Cl.
*A61K 38/21* (2006.01)
*A61K 47/60* (2017.01)
*A61P 1/16* (2006.01)
*A61P 31/14* (2006.01)

(52) U.S. Cl.
CPC .............. *A61K 38/21* (2013.01); *A61K 47/60* (2017.08); *A61P 1/16* (2018.01); *A61P 31/14* (2018.01)

(58) Field of Classification Search
None
See application file for complete search history.

(56) References Cited

U.S. PATENT DOCUMENTS

| | | |
|---|---|---|
| 6,927,040 B2 | 8/2005 | Sheppard et al. |
| 7,038,032 B2 | 5/2006 | Sheppard et al. |
| 7,135,170 B2 | 11/2006 | Klucher et al. |
| 7,157,559 B2 | 1/2007 | Brady et al. |
| 7,759,092 B2 | 7/2010 | Zamost et al. |
| 7,968,315 B2 | 6/2011 | Zamost et al. |
| 8,211,670 B2 | 7/2012 | Zamost et al. |
| 8,759,027 B2 | 6/2014 | Zamost et al. |
| 8,980,245 B2 | 3/2015 | Ho |
| 9,499,598 B2 | 11/2016 | Brady et al. |
| 2008/0090777 A1 | 4/2008 | Pearlman |
| 2011/0104105 A1 | 5/2011 | Weiner et al. |
| 2014/0134265 A1 | 5/2014 | Buggy et al. |
| 2017/0209542 A1 | 7/2017 | Brady et al. |

FOREIGN PATENT DOCUMENTS

| | | |
|---|---|---|
| JP | 2007-531741 A | 11/2007 |
| JP | 2014-525939 A | 10/2014 |
| JP | 2015-528449 A | 9/2015 |
| WO | 2011/088126 A2 | 7/2011 |
| WO | 2015/168648 A1 | 11/2015 |
| WO | 2017-079009 A1 | 5/2017 |
| WO | 2017-143253 A1 | 8/2017 |
| WO | 2020-041778 A1 | 2/2020 |

OTHER PUBLICATIONS

Kabacam et al., Turk J.Gastroenterol., (2012), vol. 23(5), pp. 560-568 (Year: 2012).*
Torres et al., 22ndconference of the Asian Pacific Association for the study of the Liver (APASL 2012), Taipei (Year: 2012).*
Giersch et al., Monothematic Conf EASL.(2013)p. 1 (Year: 2013).*
Bahcecioglu, I. et al. "Pegylated Interferon α Therapy in Chronic Delta Hepatitis: A One-Center Experience." *Hepatitis Monthly*, vol. 15, Issue 3. Published Mar. 2015. 5 pages.
Chan, H. et al. "Peginterferon Lambda for the Treatment of HBeAg-Positive Chronic Hepatitis B: A Randomized Phase 2b Study (LIRA-B)." *Journal of Hepatology*, vol. 64, issue 5. Published May 2016. pp. 1011-1019.
Giersch, K. et al. "Hepatitis B and Delta Virus: Advances on Studies about Interactions between the Two Viruses and the Infected Hepatocyte." *Journal of Clinical and Translational Hepatology*, vol. 3, Issue 3. Published Sep. 2015. pp. 220-229.
Heidrich, B. et al. "Late HDV RNA Relapse After Peginterferon Alpha-Based Therapy of Chronic Hepatitis Delta." *Hepatology—Official Journal of the American Association for the Study of Liver Diseases*. vol. 60, Issue 1. Published Jul. 2014. pp. 87-97.
International Search Report and Written Opinion received in International Patent Application No. PCT/US2017/018466 dated May 4, 2017. 12 Pages.
Wedemeyer, H. et al. "Peginterferon plus Adefovir versus Either Drug Alone for Hepatitis Delta." *The New England Journal of Medicine*. vol. 364. Published Jan. 2011. 24 pages.
Eiger Biopharmaceuticals, Inc., "A Phase 2 Study to Evaluate the Safety, Tolerability, and Pharmacodynamics of Pegylated Interferon Lambda Monotherapy in Patients With Chronic Hepatitis Delta Virus Infection (LIMT)", Jul. 27, 2018, 5 pages.
European Association for the Study of the Liver, "Novel Lambda Peg-Interferon Has Safety Edge Over Approved Peg-Interferon", Hep, Apr. 20, 2012, 5 pages.

(Continued)

*Primary Examiner* — Gary B Nickol
*Assistant Examiner* — Jegatheesan Seharaseyon
(74) *Attorney, Agent, or Firm* — Kilpatrick Townsend & Stockton

(57) ABSTRACT

Methods of treating a hepatitis delta virus (HDV) infection in a human patient are provided. In some embodiments, the method comprising administering to the patient a therapeutically effective amount of interferon lambda for at least four weeks.

24 Claims, No Drawings
Specification includes a Sequence Listing.

(56) References Cited

OTHER PUBLICATIONS

Extended European Search Report dated Dec. 6, 2019 in European Patent Application No. 17753966.5, 10 pages.
International Preliminary Report on Patentability dated Aug. 21, 2018 in International Patent Application No. PCT/US2017/018466, 6 pages.
International Search Report and Written Opinion dated Nov. 18, 2019 in International Patent Application No. PCT/US2019/048038, 26 pages.
Roche Pegasys, "Peginterferon alfa-2a", retrieved from the internet <https://www.accessdata.fda.gov/drugsatfda_docs/label/2002/pegihof120302LB.htm> on Mar. 10, 2019, 25 pages.
Squibb, B.M., et al. "Safety and Efficacy Study of Pegylated Interferon Lambda Versus Pegylated Interferon Alfa, Plus Ribavirin in Subjects With Hepatitis C", ClinicalTrials.gov, First posted Oct. 6, 2011, 7 pages.
Muir, A. J., et al., "Phase 1b Study of Pegylated Interferon Lambda 1 With or Without Ribavirin in Patients with Chronic Genotype 1 Hepatitis C Virus Infection", Hepatology, vol. 52, No. 3, DOI:10.1002/hep.23743, Sep. 1, 2010, p. 822-832.
Etzion, O., et al. "PS-052: End of Study Results from LIMT HDV Study: 36% Durable Virologic Response at 24 Weeks Post-Treatment with Pegylated Interferon Lambda Monotheraphy in Patients with Chronic Hepatitis Delta Virus Infection", Journal of Hepatology, vol. 70, No. Supplement 1, European Association for the Study of the Liver (EASL), Apr. 10-14, 2019, XP009516780, 17 pages.
Giersch, K., et al. "Both interferon alpha and lambda can reduce all intrahepatic HDV infection markers in HBV/HDV infected humanized mice", Scientific Reports, vol. 7, No. 1, DOI: https://doi.org/10.1038/s41598-017-03946-9, XP055636233, Jun. 16, 2017, 11 pages.
Etzion, O., et al., "Noninvasive Tests for Detection of Biopsy-proven Cirrhosis in Chronic Hepatitis D Infected Patients Are Suboptimal", American Association for the Study of Liver Diseases (AASLD), The Liver Meeting Digital Experience (TLMdX) 2020, hosted Nov. 13-16, 2020, 1 page.
Yardeni, D., et al, Regression of Liver Fibrosis Following 48 Weeks of Therapy with Peginterferon Lambda in Patients with Chronic Hepatitis Delta Virus (HDV) Infection, American Association for the Study of Liver Diseases (AASLD), The Liver Meeting Digital Experience (TLMdX) 2020, hosted Nov. 13-16, 2020, 1 page.

\* cited by examiner

TREATMENT OF HEPATITIS DELTA VIRUS INFECTION WITH INTERFERON LAMBDA

CROSS-REFERENCE TO RELATED APPLICATIONS

This application is a national stage application under 35 U.S.C. § 371 of International Application No. PCT/US2017/018466, filed Feb. 17, 2017, which claims priority to U.S. Provisional Application No. 62/297,759, filed Feb. 19, 2016, the entire content of each of which is incorporated by reference herein.

SEQUENCE LISTING

The instant application contains a Sequence Listing which has been filed electronically in ASCII format and is hereby incorporated by reference in its entirety. Said ASCII copy, created on Jul. 10, 2019, is named 1093576SequenceListing.txt and is 2,023 bytes in size.

FIELD OF INVENTION

The present invention provides methods for treating viral hepatitis resulting from Hepatitis delta virus (HDV) infection, and so relates to the fields of chemistry, medicinal chemistry, medicine, molecular biology, and pharmacology.

BACKGROUND OF THE INVENTION

Hepatitis delta virus (HDV) causes the most severe form of chronic viral hepatitis, and there is no effective medical therapy. HDV always presents as a co-infection with hepatitis B virus (HBV). Chronic HDV and HBV co-infection worsens preexisting HBV-related liver damage and leads to liver cirrhosis, hepatic decompensation, and hepatocellular carcinoma. See, Negro, *Cold Spring Harb Perspect Med*, 2014, 4:a021550; Höner zu Siederdissen, *Visc Med*, 2016, 32:86-94; Lau, *Hepotology*, 1999, 30:546-549. Patients who are co-infected with both HDV and HBV are more likely to die of complications from liver disease compared to patients infected with HBV alone. See, Alavian et al., *J Res Med Sci*, 2012, 17:967-974.

Interferon alfa therapy has been described for the treatment of HDV. However, a sustained virological response with interferon alfa therapy is achieved in only about 30% of patients, and only a minority of patients clear HDV infection. Giersch and Dandri, *Journal of Clinical and Translational Hepatology*, 2015, 3:220-229; Bahcecioglu et al., *Hepat Mon.*, 2015, 15(e):e24366. Interferon alpha mediates its effects by signaling through interferon alpha receptors that are widely expressed by many different cell types. In contrast to interferon alpha, interferon lambda signals through a different class of receptors, the interferon lambda receptors, that have a restricted cellular expression pattern. Interferon lambda also exhibits distinct antiviral activities from interferon alpha, due in part to the differences in expression of the interferon receptors. In a comparative study of pegylated interferon alfa and a pegylated interferon lambda for the treatment of HBV (Chan et al., *J. Hepatology*, 2016, 64:1011-1019), it was found that although pegylated interferon lambda produced more pronounced declines in viremia as compared to pegylated interferon alfa at the midpoint of treatment (24 weeks), by the end of the treatment period there was no difference between pegylated interferon alfa and pegylated interferon lambda treatment, and post-treatment there was a greater virologic rebound in the pegylated interferon lambda treatment group. HBV/HDV co-infected mice receiving pegylated interferon alfa for four weeks exhibited a 2.2 log reduction in HDV-RNA levels, while mice receiving pegylated interferon lambda for four weeks exhibited a 1.5 log reduction in HDV-RNA levels (Giersch et al., 2013). To date, the efficacy of long-term pegylated interferon lambda therapy for the treatment of HDV has not been described. There continues to be an ongoing need for agents to treat HDV infection.

BRIEF SUMMARY OF THE INVENTION

In one aspect, methods of treating a hepatitis delta virus (HDV) infection in a human patient are provided. In some embodiments, the method comprises administering to the patient a therapeutically effective amount of interferon lambda for at least four weeks. In some embodiments, the method comprises administering to the patient a therapeutically effective amount of interferon lambda-1a for at least four weeks. In some embodiments, the method comprises administering to the patient a therapeutically effective amount of pegylated interferon lambda (e.g., pegylated interferon lambda-1a) for at least four weeks.

In some embodiments, the interferon lambda (e.g., pegylated interferon lambda, e.g., pegylated interferon lambda-1a) is subcutaneously administered. In some embodiments, the interferon lambda (e.g., pegylated interferon lambda, e.g., pegylated interferon lambda-1a) is administered weekly as a subcutaneous injection. In some embodiments, the interferon lambda (e.g., pegylated interferon lambda, e.g., pegylated interferon lambda-1a) is administered at a dose of 120 micrograms per week. In some embodiments, the interferon lambda (e.g., pegylated interferon lambda, e.g., pegylated interferon lambda-1a) is administered at a dose of 180 micrograms per week.

In some embodiments, the patient to be treated has compensated liver disease with or without cirrhosis. In some embodiments, the patient to be treated has compensated liver disease with cirrhosis.

In some embodiments, the interferon lambda (e.g., pegylated interferon lambda, e.g., pegylated interferon lambda-1a) is administered to the patient in a course of therapy extending at least 30 days, at least 60 days, at least 90 days, at least 120 days, at least 150 days, or at least 180 days; or at least 4 weeks, at least 8 weeks, at least 12 weeks, at least 16 weeks, at least 20 weeks, or at least 24 weeks. In some embodiments, the interferon lambda (e.g., pegylated interferon lambda, e.g., pegylated interferon lambda-1a) is administered to the patient for at least 6 months, at least 9 months, at least one year, at least 18 months, at least 2 years, or longer. In some embodiments, the interferon lambda (e.g., pegylated interferon lambda, e.g., pegylated interferon lambda-1a) is administered for at least 48 weeks, at least 60 weeks, at least 72 weeks, at least 84 weeks, or at least 96 weeks.

In some embodiments, interferon lambda (e.g., interferon lambda-1a) is administered as a subcutaneous injection at a dose of 120 micrograms per week for at least 12 weeks to a patient with chronic HDV infection. In some embodiments, interferon lambda (e.g., interferon lambda-1a) is administered as a subcutaneous injection at a dose of 120 micrograms per week for at least 24 weeks to a patient with chronic HDV infection. In some embodiments, interferon lambda (e.g., interferon lambda-1a) is administered as a subcutaneous injection at a dose of 120 micrograms per week for 48 weeks to a patient with chronic HDV infection. In some embodiments, interferon lambda (e.g., interferon lambda-1a) is administered as a subcutaneous injection at a dose of 120 micrograms per week for 96 weeks to a patient with chronic HDV infection. In some embodiments, the patient with chronic HDV infection has compensated liver disease.

In some embodiments, interferon lambda (e.g., pegylated interferon lambda, e.g., pegylated interferon lambda-1a) is administered as a subcutaneous injection at a dose of 120 micrograms per week for at least 12 weeks to a patient with chronic HDV infection. In some embodiments, interferon lambda (e.g., pegylated interferon lambda, e.g., pegylated interferon lambda-1a) is administered as a subcutaneous injection at a dose of 120 micrograms per week for at least 24 weeks to a patient with chronic HDV infection. In some embodiments, interferon lambda (e.g., pegylated interferon lambda, e.g., pegylated interferon lambda-1a) is administered as a subcutaneous injection at a dose of 120 micrograms per week for 48 weeks to a patient with chronic HDV infection. In some embodiments, interferon lambda (e.g., pegylated interferon lambda, e.g., pegylated interferon lambda-1a) is administered as a subcutaneous injection at a dose of 120 micrograms per week for 96 weeks to a patient with chronic HDV infection. In some embodiments, the patient with chronic HDV infection has compensated liver disease.

In some embodiments, interferon lambda (e.g., interferon lambda-1a) is administered as a subcutaneous injection at a dose of 180 micrograms per week for at least 12 weeks to a patient with chronic HDV infection. In some embodiments, interferon lambda (e.g., interferon lambda-1a) is administered as a subcutaneous injection at a dose of 180 micrograms per week for at least 24 weeks to a patient with chronic HDV infection. In some embodiments, interferon lambda (e.g., interferon lambda-1a) is administered as a subcutaneous injection at a dose of 180 micrograms per week for 48 weeks to a patient with chronic HDV infection. In some embodiments, interferon lambda (e.g., interferon lambda-1a) is administered as a subcutaneous injection at a dose of 180 micrograms per week for 96 weeks to a patient with chronic HDV infection. In some embodiments, the patient with chronic HDV infection has compensated liver disease.

In some embodiments, pegylated interferon lambda (e.g., pegylated interferon lambda-1a) is administered as a subcutaneous injection at a dose of 180 micrograms per week for at least 12 weeks to a patient with chronic HDV infection. In some embodiments, pegylated interferon lambda (e.g., pegylated interferon lambda-1a) is administered as a subcutaneous injection at a dose of 180 micrograms per week for at least 24 weeks to a patient with chronic HDV infection. In some embodiments, pegylated interferon lambda (e.g., pegylated interferon lambda-1a) is administered as a subcutaneous injection at a dose of 180 micrograms per week for 48 weeks to a patient with chronic HDV infection. In some embodiments, pegylated interferon lambda (e.g., pegylated interferon lambda-1a) is administered as a subcutaneous injection at a dose of 180 micrograms per week for 96 weeks to a patient with chronic HDV infection. In some embodiments, the patient with chronic HDV infection has compensated liver disease.

In some embodiments, the course of treatment results in an HDV viral load that is below 100 copies/mL serum or below 100 IU/mL serum. In some embodiments, the HDV viral load remains below 100 copies/mL serum or below 100 IU/mL serum for at least 12 weeks after the end of treatment. In some embodiments, the HDV viral load remains below 100 copies/mL serum or below 100 IU/mL serum for at least 24 weeks after the end of treatment.

In some embodiments, the course of treatment results in an HDV viral load that is below the level of detection. In some embodiments, the HDV viral load remains below the level of detection for at least 12 weeks after the end of treatment. In some embodiments, the HDV viral load remains below the level of detection for at least 24 weeks after the end of treatment.

In some embodiments, the course of treatment results in improved liver function in the patient. In some embodiments, the improved liver function is an improvement in one or more serum markers selected from the group consisting of serum albumin, bilirubin, alanine aminotransferase (ALT), aspartate aminotransferase (AST), prothrombin, alfa2-macroglobulin, apolipoproteinA1, haptoglobin, gamma-glutamyl transpeptidase (GGT). In some embodiments, the improved liver function is an improvement in liver fibrosis.

In some embodiments, the method further comprises administering to the patient an additional antiviral therapeutic agent or agents as cotherapy. In some embodiments interferon lambda therapy is the sole or primary antiviral therapy administered to the patient. In some embodiments interferon lambda (e.g., pegylated interferon lambda, e.g., pegylated interferon lambda-1a) therapy is the sole or primary anti-HDV therapy administered to the patient. In some embodiments, interferon lambda (e.g., pegylated interferon lambda, e.g., pegylated interferon lambda-1a) therapy is the sole or primary antiviral therapy administered to the patient. In some embodiments, the patient receives one or more antiviral or anti-HDV therapeutics in addition to interferon lambda (e.g., pegylated interferon lambda, e.g., pegylated interferon lambda-1a).

These and other aspects and embodiments of the invention are described in more detail below.

DETAILED DESCRIPTION OF THE INVENTION

I. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

The singular forms "a," "an," and "the" include plural referents unless the context clearly dictates otherwise. Thus, for example, reference to "a compound" includes a plurality of compounds.

The term "administration" refers to introducing a compound, a composition, or an agent of the present disclosure into a host, such as a human. In the context of the present invention, one preferred route of administration of the agents is subcutaneous administration. Other routes are intravenous administration and oral administration.

The term "baseline," unless otherwise specified or apparent from context, refers to a measurement (of, e.g., viral load, patient condition, ALT level) made prior to a course of therapy.

The term "comprising" is intended to mean that the compounds, compositions and methods include the recited elements, but does not exclude others. "Consisting essentially of" when used to define compounds, compositions and methods, shall mean excluding other elements that would materially affect the basic and novel characteristics of the claimed invention. Embodiments defined by each of these transition terms are within the scope of this invention.

The terms "course of treatment" and "course of therapy" are used interchangeably herein, and refer to the medical interventions made after a patient is diagnosed, e.g., as being infected with HDV and in need of medical intervention. Medical interventions include, without limitation, the administration of drugs for a period of time, typically, for HDV infected patients, at least one and typically several or many months or even years.

The term "HDV RNA viral load" or "viral load" of a human serum or plasma sample refers to the amount of HDV RNA in a given amount of a human serum or plasma sample. HDV RNA is generally detected by quantitative real-time reverse transcription-polymerase chain reaction (qRT-PCR) assays. In such assays, the amount of signal generated during the assay is proportional to the amount of HDV RNA in the sample. The signal from the test sample is compared to that of a dilution series of a quantified Hepatitis Delta RNA standard, and a copy number of genome copies is calculated. See, e.g., Kodani et al., 2013, J. Virol. Methods, 193(2), 531; Karatayli et al., 2014, J. Clin. Virol, 60(1), 11. HDV RNA viral load may be reported as RNA copies per mL serum (or plasma) or using International Units (IU) per mL serum (or plasma). See, Chudy et al., 2013, Collaborative Study to establish a World Health Organization International standard for hepatitis D virus RNA for nucleic acid amplification technique (NAT)-based assays." WHO Expert Committee on Biological Standardization WHO/BS/2013.2227. A commercially available assay is available from ARUP Laboratories (Salt Lake City, Utah). The limit of detection for the ARUP HDV RNA assay has been reported to be 31 IU/mL. Analytik Jena AG (Germany) offers the RoboGene® HDV RNA Quantification Kit 2.0, which is CE-IVD certified with WHO standard references to assess the response to antiviral treatment. The limit of detection for the RoboGene® assay is reported to be 6 IU/mL. Reference to a "viral load" without specified units (e.g., "a viral load of less than 100") refers to copies of HDV RNA per mL serum, unless otherwise indicated or apparent from context. Unless otherwise specified, reference to "below the level of detection" means below 15 IU/mL.

HDV levels are generally presented using $\log_{10}$ units, following the normal conventions of virology. HDV RNA levels may be presented in units of "RNA copies per mL" or as "International Units (IU) per mL." See, Chudy et al., 2013, Collaborative Study to establish a World Health Organization International standard for hepatitis D virus RNA for nucleic acid amplification technique (NAT)-based assays." WHO Expert Committee on Biological Standardization WHO/BS/2013.2227. Both units are used in this specification. As used herein, recitation of "HDV RNA copies per mL," (when not otherwise specified and not including discussions related to clinical trial results, e.g., as presented in the examples) should be read, for purposes of written description or basis, as referring to "HDV RNA copies/mL or [in the alternative] HDV IU/mL." Where a specific quantity of HDV RNA copies per mL is recited, a multiplier of 1.2 may be applied, for the purposes of written description and support, to convert the quantity of HDV RNA copies/mL to the quantity of IU/mL. For example, "120 HDV RNA copies per mL" should be read as "120 copies/mL or 100 IU/mL."

Changes in HDV RNA levels may be represented as a "log reduction" following the normal conventions of virology. For example, a 1 log reduction (i.e., −1 log) in viral load (e.g., from 7 log to 6 log) is a 10-fold reduction, and a 2 log reduction (i.e., −2 log) in viral load (e.g., from 7 log to 5 log) is a 100-fold reduction. A reduction from 4 log RNA copies/mL to 3 log RNA copies/mL is equivalent to a reduction from 4 log IU/mL to 3 log IU/mL.

The term "HDV infection" with respect to a human (host) refers to the fact that the host is suffering from HDV infection. Typically, an HDV infected human host will have a viral load of HDV RNA of at least about 2 log HDV RNA copies/mL of host serum or plasma or $10^2$ copies of HDV-RNA/mL of host serum or plasma, often at least about 3 log HDV RNA copies/mL of host serum or plasma or $10^3$ copies of HDV-RNA/mL of host serum or plasma, and, often, especially for patients not on any therapy, at least about 4 log HDV RNA copies/mL of host serum or plasma or $10^4$ copies of HDV-RNA/mL of host serum or plasma, such as about 4 log HDV RNA copies/mL of host serum or plasma to 8 log HDV RNA copies/mL of host serum or plasma or $10^4$-$10^8$ copies of HDV-RNA/mL of host serum or plasma. As used herein, the term "chronic HDV infection" with respect to a human host refers to an HDV infection that has persisted in the human host for at least 6 months, as documented by a positive HDV antibody (Ab) test and/or detectable HDV RNA by qRT-PCR. Diagnosis and pathogenesis of HDV is described, for example, in Wedemeyer et al., *Nat. Rev. Gastroenterol. Hepotol*, 2010, 7:31-40.

The term "Lower Limit of Quantification" refers to the lowest concentration of a substance of analyte (e.g., a viral titer) that can be reliably quantified by a particular assay within a stated confidence limit.

The terms "patient", "host," or "subject," are used interchangeably and refer to a human infected with HDV, including patients previously infected with HDV in whom virus has cleared.

The term "pharmaceutical composition" is meant to encompass a composition suitable for administration to a subject. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intratracheal, intramuscular, subcutaneous, inhalational, and the like.

The term "therapeutically effective amount" as used herein refers to that amount of an embodiment of the agent (e.g., a compound, inhibitory agent, or drug) being administered that will treat to some extent a disease, disorder, or condition, e.g., relieve one or more of the symptoms of the disease, i.e., infection, being treated, and/or that amount that will prevent, to some extent, one or more of the symptoms of the disease, i.e., infection, that the subject being treated has or is at risk of developing.

The terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a human subject, and includes: (a) reducing the risk of occurrence of the disease in a subject determined to be predisposed to the disease but not yet diagnosed as infected with the disease, (b) impeding the development of the disease, and/or (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of an agent that provides for enhanced or desirable effects in the subject (e.g., reduction of viral load, reduction of disease symptoms, etc.).

The terms "undetectable" or "below the level of detection," as used with reference to HDV RNA levels, means that no HDV RNA copies can be detected by the assay methodology employed. In some embodiments, the assay is quantitative RT-PCR.

II. Methods of Treatment

In one aspect, methods for the treatment of HDV infection, in which the HDV-infected patient is treated by administration of interferon lambda, are provided. In some embodiments, a pegylated form of interferon lambda is administered. In some embodiments, patients receiving interferon lambda therapy (e.g., pegylated interferon lambda therapy) are also treated with the antiviral nucleotide or nucleoside analog (e.g., an anti-HBV nucleotide or nucleoside analog).

In another aspect, methods for the treatment of HBV, in which the HBV-infected patient is treated by administration of interferon lambda, are provided. In some embodiments, a pegylated form of interferon lambda is administered. In some embodiments, the HBV-infected patient receiving interferon lambda therapy (e.g., pegylated interferon lambda therapy) are also treated with the antiviral nucleotide or nucleoside analog (e.g., an anti-HBV nucleotide or nucleoside analog). In some embodiments, a patient who is infected with HBV is not co-infected with HDV.

Interferon Lambda Therapy

Interferons are polypeptides that inhibit viral replication and cellular proliferation and modulate immune response. Based on the type of receptor through which they signal, human interferons have been classified into three major types (Types I, II, and III). All type I IFNs bind to a specific cell surface receptor complex known as the IFN-alpha receptor (IFNAR) that consists of IFNAR1 and IFNAR2 chains. The type I interferons present in humans are IFN-alpha, IFN-beta, IFN-epsilon, and IFN-omega. Type II IFNs bind to IFN-gamma receptor (IFNGR) that consists of IFNGR1 and IFNGR2 chains. The type II interferon in humans is IFN-gamma. The type III interferon group consists of three IFN-lambda molecules called IFN-lambda1, IFN-lambda2 and IFN-lambda3 (also called IL29, IL28A, and IL28B, respectively). These IFNs signal through a receptor complex consisting of IL10R2 (also called CRF2-4) and IFNLR1 (also called CRF2-12).

The term "interferon-lambda" or "IFN-λ" as used herein includes naturally occurring IFN-λ; synthetic IFN-λ; derivatized IFN-λ (e.g., PEGylated IFN-λ, glycosylated IFN-λ, and the like); and analogs of naturally occurring or synthetic IFN-λ. In some embodiments, an IFN-λ is a derivative of IFN-λ that is derivatized (e.g., chemically modified relative to the naturally occurring peptide) to alter certain properties such as serum half-life. As such, the term "IFN-λ" includes IFN-λ derivatized with polyethylene glycol ("PEGylated IFN-λ"), and the like. PEGylated IFN-λ (e.g., PEGylated IFN-λ-1a), and methods for making same, is discussed in, e.g., U.S. Pat. Nos. 6,927,040, 7,038,032, 7,135,170, 7,157,559, and 8,980,245; and PCT publication Nos. WO 2005/097165, WO 2007/012033, WO 2007/013944 and WO 2007/041713; all of which are herein incorporated by reference in their entirety. In some embodiments, the pegylated IFN-λ-1a has the structure described in U.S. Pat. No. 7,157,559, which is incorporated by reference herein in its entirety.

In some embodiments, an interferon for use in a therapeutic method as described herein is a pegylated IFN-λ1 (e.g., pegylated IFN-λ-1a), pegylated IFN-λ-2, or pegylated IFN-λ-3.

In some embodiments, the pegylated IFN-λ1 has the amino acid sequence shown below (lines show intrachain disulfide bonds) (SEQ ID NO: 1):

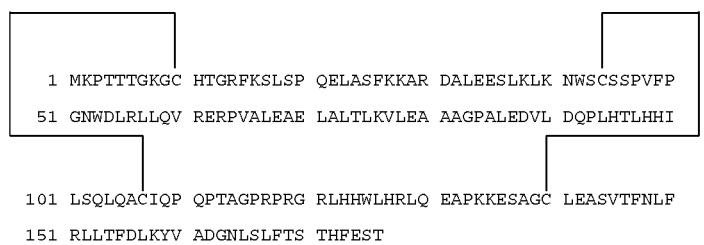

```
  1 MKPTTTGKGC HTGRFKSLSP QELASFKKAR DALEESLKLK NWSCSSPVFP
 51 GNWDLRLLQV RERPVALEAE LALTLKVLEA AAGPALEDVL DQPLHTLHHI
101 LSQLQACIQP QPTAGPRPRG RLHHWLHRLQ EAPKKESAGC LEASVTFNLF
151 RLLTFDLKYV ADGNLSLFTS THFEST
```

Patient Population

In some embodiments, a patient to be treated with interferon lambda therapy as described herein is a patient having a chronic HDV infection. In some embodiments, the patient to be treated has a chronic HDV infection of at least 6 months duration documented by a positive HDV antibody (Ab) test, and/or detectable HDV RNA by qRT-PCR. In some embodiments, a patient to be treated with a therapeutic method described herein is a patient having an acute HDV infection, one that is newly diagnosed or otherwise believed not to have existed in the patient for more than six months. Diagnosis and pathogenesis of HDV is described, for example, in Wedemeyer et al., *Not. Rev. Gastroenterol. Hepotol,* 2010, 7:31-40. HDV is known to exist in a variety of subtypes; the methods described herein are suitable for treating all HDV patients, regardless of HDV subtype. In some embodiments, the patient is an adult (18 years or older).

In some embodiments, a patient to be treated has a baseline viral load of at least $10^2$ HDV RNA copies per mL serum or plasma or at least $10^2$ IU/mL serum or plasma, e.g., at least $10^3$ HDV RNA copies per mL or at least $10^3$ IU/mL serum or plasma, at least $10^4$ HDV RNA copies per mL or at least $10^4$ IU/mL serum or plasma, at least $10^5$ HDV RNA copies per mL or at least $10^5$ IU/mL serum or plasma, at least $10^6$ HDV RNA copies per mL or at least $10^6$ IU/mL serum or plasma, at least $10^7$ HDV RNA copies per mL or at least $10^7$ IU/mL serum or plasma, or at least $10^8$ HDV RNA copies per mL or at least $10^8$ IU/mL serum or plasma. In some embodiments, HDV viral load is measured using serum samples from the patient. In some embodiments, HDV viral load is measured using plasma samples from the patient. In some embodiments, viral load is measured by quantitative RT-PCR. qRT-PCR assays for quantification of HDV RNA in serum or plasma are known in the art, e.g., as described above.

In some embodiments, a patient to be treated exhibits one or more symptoms of liver dysfunction. In some embodiments, the patient exhibits one or more liver function parameters that are outside the normal parameters for a healthy control (e.g., a subject that is not infected with HDV or HBV). In some embodiments, the liver function parameter is selected from the group consisting of serum albumin, bilirubin, alanine aminotransferase (ALT), aspartate aminotransferase (AST), and prothrombin activity. In some embodiments, the patient has a serum ALT level that is at least two-fold higher than the upper limit of normal (ULN) (e.g., at least 2-fold, at least 3-fold, at least 4-fold, at least 5-fold, at least 6-fold, at least 7-fold, at least 8-fold, at least 10-fold or higher than the ULN). Liver function parameters are described in the art. See, e.g., Limdi et al., Postgrad Med J, 2003, 79:307-312. Methods of measuring these liver function parameters are known in the art and are also commercially available.

In some embodiments, the patient has compensated liver disease (e.g., as classified according to the Child-Turcotte-Pugh Classification System) with or without liver cirrhosis. It will be recognized by a person of ordinary skill in the art that the Child-Turcotte-Pugh Classification System is used to classify the severity of liver disease and is determined by assessing serum albumin levels, bilirubin levels, international normalized ratio of prothrombin time levels, ascites formation, and encephalopathy. In some embodiments, the patient has a Child-Turcotte-Pugh score of 5-6 (class A). In some embodiments, the patient has compensated liver disease with liver cirrhosis. In some embodiments, the patient has compensated liver disease without liver cirrhosis.

In some embodiments, the patient is diagnosed with chronic hepatitis as determined by liver biopsy within 6 months before treatment. In some embodiments, the patient has evidence of chronic hepatitis based on a liver biopsy within 6 months before screening. In some embodiments, the patient has a serum alanine aminotransferase (ALT) level that is above the upper limit of normal (ULN) within 24 weeks prior to treatment and/or at the initiation of treatment.

In various embodiments, the patient meets one or more independently selected eligibility criteria in Example 1.

Duration of Treatment and Treatment Endpoints

Patients may receive interferon lambda therapy for a predetermined time, an indefinite time, or until an endpoint is reached. Treatment may be continued on a continuous daily basis for at least two to three months. In some embodiments, therapy is for at least 30 days, at least 60 days, at least 90 days, at least 120 days, at least 150 days, or at least 180 days. In some embodiments, treatment is continued for at least 6 months, at least 7 months, at least 8 months, at least 9 months, at least 10 months, at least 11 months, at least one year, at least 15 months, at least 18 months, or at least 2 years. In some embodiments, therapy is for at least 6 weeks, 12 weeks, 18 weeks, 24 weeks, 30 weeks, 36 weeks, 42 weeks, 48 weeks, 60 weeks, 72 weeks, 84 weeks, or 96 weeks. In other embodiments, treatment is continued for the rest of the patient's life or until administration is no longer effective in maintaining the virus at a sufficiently low level to provide meaningful therapeutic benefit.

In accordance with the methods of the invention, some HDV patients will respond to therapy as described herein by clearing virus to undetectable levels, after which treatment may be suspended unless and until the HDV levels return to detectable levels. Other patients will experience a reduction in viral load and improvement of symptoms but will not clear the virus to undetectable levels but will remain on "long term therapy" for a defined period of time (e.g., for about 1 year or for about 2 years) or so long as it provides therapeutic benefit.

In some embodiments, treatment with interferon lambda therapy results in a reduction of HDV viral load in the patient of at least 1.5 log HDV RNA copies/mL serum when measured after 8 weeks of treatment. In some embodiments, treatment with interferon lambda therapy results in a reduction of HDV viral load in the patient of at least 2.0 log HDV RNA copies/mL serum when measured after 8 weeks of treatment. In some embodiments, treatment with interferon lambda therapy results in a reduction of HDV viral load in the patient of at least 2.5 log HDV RNA copies/mL serum when measured after 8 weeks of treatment.

In some embodiments, treatment with interferon lambda therapy results in a sustained reduction of HDV viral load (e.g., a decrease of at least 1.5 log HDV RNA copies/mL serum, at least 2.0 log HDV RNA copies/mL serum or at least 2.5 log HDV RNA copies/mL serum, or a decrease in HDV RNA to undetectable levels) that is sustained for a period of time (e.g., 1 month, 3 months, 6 months, 1 year or longer) while the course of treatment is still ongoing. In some embodiments, treatment with interferon lambda therapy results in a sustained reduction of HDV viral load that is sustained for a period of time (e.g., 1 month, 3 months, 6 months, 1 year or longer) after the course of treatment is finished. In some embodiments, the course of treatment results in HDV RNA levels (e.g., serum HDV RNA levels or plasma HDV RNA levels) below 1,000 copies/mL. In some embodiments, the HDV RNA levels remain below 1,000 copies/mL for at least one month, at least three months, at least one year, or longer. In some embodiments, the course of treatment results in HDV RNA levels (e.g., serum HDV RNA levels or plasma HDV RNA levels) below 100 copies/mL. In some embodiments, the HDV RNA levels remain below 100 copies/mL for at least one month, at least three months, at least one year, or longer. The phrase "remains below" an initial measured value (e.g., 100 copies/mL or 100 IU/mL) for 1 month (or another specified time) means that a viral load measurement taken at least 1 month (or at the other specified time) after determination of the initial measured value is no higher than the initial value. In some embodiments, the patient does not receive interferon lambda therapy during the specified time. In some embodiments, the patient does not receive any anti-HDV treatment during the specified time.

In some embodiments, therapy as disclosed herein is continued for a period of time until HDV RNA levels are below 3 log HDV RNA copies/mL (below 1,000 copies/mL), or sometimes until HDV RNA levels are below 2 log HDV RNA copies/mL (below 100 copies/mL) or below the level of detection. In some cases therapy may be continued for a period of time (such as 1 to 3 months or longer) after viral load has dropped to acceptably low levels (e.g., undetectable levels). In some embodiments, therapy is continued until the HDV viral load is reduced to undetectable levels.

In some embodiments, a patient treated according to the methods described herein exhibits a reduction in HDV viral load to undetectable levels during the course of treatment, and the patient maintains the reduction in HDV viral load to undetectable levels for at least 12 weeks after the end of treatment. In some embodiments, a patient treated according to the methods described herein exhibits a reduction in HDV viral load to undetectable levels during the course of treatment, and the patient maintains the reduction in HDV viral load to undetectable levels for at least 24 weeks after the end of treatment.

In some embodiments, the patient's HDV titer rises from baseline prior to dropping below baseline during the course of treatment. In some embodiments, the patient's HDV level rises to more than 150% of baseline, or more than 200% of baseline. In some embodiments, the rise in the titer occurs within 2 weeks after initiation of therapy. In some embodiments, the patient's elevated HDV titer drops to below baseline within 2 weeks, or within 3 weeks, of initiation of therapy.

In some embodiments, a patient treated according to the methods described herein exhibits an improvement in one or more liver function parameters. In some embodiments, the improved liver function is an improvement in one or more serum markers (e.g., one, two, three, four, five, six or more markers), such as serum albumin, bilirubin, alanine aminotransferase (ALT), aspartate aminotransferase (AST), prothrombin, alfa2-macroglobulin, apolipoproteinA1, haptoglobin, gamma-glutamyl transpeptidase (GGT). In some embodiments, a patient treated according to the methods described herein exhibits an improvement in liver fibrosis (e.g., as assessed by biopsy with histological analysis, transient ultrasound elastography (e.g., FibroScan), or magnetic resonance elastography). In some embodiments, treatment results in an improvement of at least 10%, at least 20%, at least 30%, at least 40%, at least 50% or more in one or more liver function parameters (e.g., an improvement in serum marker(s) or an improvement in liver fibrosis) in the patient as compared to prior to the onset of treatment. In some embodiments, treatment results in an improvement in one or more liver function parameters (e.g., an improvement in serum marker(s) or an improvement in liver fibrosis) to the level of a healthy control subject that is not infected with HDV or HBV. In some embodiments, the patient exhibits an improvement in serum ALT levels to a level that is within the upper limit of normal.

In some embodiments, a patient treated according to the methods described herein exhibits a reduction in HBV viral load compared to the baseline level at the initiation of treatment and/or compared to a similarly infected patient not receiving treatment effective to reduce the patient's HDV viral load. In some embodiments, treatment results in a reduction of at least 1 log in HBV viral load.

In some embodiments, a patient treated according to the methods described herein exhibits an improvement in one or more parameters described in Example 1. In some embodiments, patients treated according to the methods of the invention exhibit a reduction in HDV and/or HBV viral load. Prior to treatment, the patient's HDV and/or HBV viral load is measured to determine the baseline viral load. After a period of treatment (e.g., after 12 weeks of treatment), the patient's viral load is reduced compared to baseline. In some embodiments, after a period of treatment (e.g., after 12 weeks of treatment), the patient's viral load is substantially reduced compared to baseline, such as to very low levels or to an undetectable level. In some embodiments, treatment results in an at least 2 log reduction of HBV viral load. In some embodiments, patients treated according to the methods described herein exhibit a reduction in HBsAg levels or an improvement in clearance of HBsAg antigen. Prior to treatment the patient's HBsAg level is measured to determine a baseline. After a period of treatment (e.g., after 12 weeks of treatment), the patient's HBsAg level is reduced compared to baseline. In some embodiments, patients treated according to the methods described herein exhibits the presence of anti-HBs antibody.

Dose Escalation and Dose Reduction

In some embodiments, a patient being treated for HDV infection receives an adjustment in the dosing regimen of the interferon lambda therapy during the course of treatment. In some embodiments, the patient receives an escalating dosage regimen of interferon lambda, in that one or more later doses is a higher dose than one or more earlier doses. In some embodiments, an escalating dosage regimen may increase the patient's tolerance to the drug and minimize side effects. In some embodiments, dose escalation comprises administering interferon lambda at a dose of 120 micrograms per week for a first treatment period followed by administering interferon lambda at a dose of 180 micrograms per week for a second treatment period. In some embodiments, the length of time for the first treatment period is the same as the length of time for the second treatment period. In some embodiments, the first treatment period and the second treatment period are different lengths of time. In some embodiments, dose escalation further comprises administering one or more additional doses of interferon lambda for one or more additional treatment periods.

In some embodiments, the patient receives a dose reduction of interferon lambda, in that one or more later doses is a lower dose than one or more earlier doses. In some embodiments, dose reduction is prescribed if the patient exhibits unacceptable side effects. In some embodiments, the interferon lambda therapy comprises administering interferon lambda at a dose of 180 micrograms per week for a first treatment period followed by administering interferon lambda at a dose of 120 micrograms per week for a second treatment period. In some embodiments, the interferon lambda therapy comprises administering interferon lambda at a dose of 120 micrograms per week for a first treatment period followed by administering interferon lambda at a dose of 80 micrograms per week for a second treatment period. In some embodiments, the length of time for the first treatment period is the same as the length of time for the second treatment period. In some embodiments, the first treatment period and the second treatment period are different lengths of time.

Formulation and Administration

Interferon lambda may be administered at any therapeutically appropriate dose. In some embodiments, interferon lambda is administered at a dose of 80 micrograms (mcg) QW. In some embodiments, interferon lambda is administered at a dose of 120 mcg QW. In some embodiments, interferon lambda is administered at a dose of 180 mcg QW.

Interferon lambda may be formulated for administration by any therapeutically appropriate route. In some embodiments, interferon lambda is formulated for administration by intravenous or subcutaneous administration. Other routes suitable for drug delivery, including systemic and localized routes of administration may be used.

In certain embodiments, interferon lambda is administered by subcutaneous injection, including but not limited to injection in the thigh or abdomen. The invention provides pharmaceutical formulations in which interferon lambda can be formulated into preparations for injection in accordance with the invention by dissolving, suspending or emulsifying it in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Unit dosage forms for injection or intravenous administration may comprise in a composition as a solution in sterile water, normal saline or another pharmaceutically acceptable carrier. Appropriate amounts of the active pharmaceutical ingredient for unit dose forms of interferon lambda are provided herein.

In some embodiments, interferon lambda (e.g., an interferon lambda 1 such as interferon lambda 1a) or an analog thereof is formulated and/or administered and/or modified as described in one of the following patent publications, incorporated by reference herein: U.S. Pat. Nos. 6,927,040, 7,038,032, 7,135,170, 7,157,559, and 8,980,245, US 2009/0326204, US 2010/0222266, US 2011/0172170, or US 2012/0036590.

III. Examples

The following examples are provided to illustrate, but not to limit, the claimed invention.

Example 1. Protocol Synopsis for Treating HDV Patients with Pegylated Interferon Lambda This example describes a Phase 2 clinical study protocol for evaluating the safety, tolerability, and pharmacodynamics of pegylated interferon lambda monotherapy in patients with chronic HDV infection.

TABLE 1

| | |
|---|---|
| Sponsor | Eiger BioPharmaceuticals, Inc. (United States) |
| Product | Pegylated interferon lambda-1a (PEG-IFN-λ) |
| Title | A Phase 2 study to evaluate the safety, tolerability, and pharmacodynaMics of pegylaTed interferon lambda monotherapy in patients with chronic hepatitis D virus infection (LIMT) |
| Study phase | Phase 2 |
| Study center(s) | Approximately 6 centers in the United States, New Zealand, Pakistan, and Israel |
| Indication | Chronic hepatitis D viral infection |
| Primary objectives | To evaluate the safety and tolerability of treatment with 2 dose levels of Lambda over a 48-week treatment period<br>To evaluate the proportion of patients with undetectable HDV RNA 12 weeks after the end of treatment |
| Secondary objectives | To evaluate the effect of treatment with 2 dose levels of Lambda on the following:<br>   HDV levels<br>   ALT levels<br>   Hepatitis B surface antigen (HbsAg) levels |
| Exploratory objective | To evaluate the effects of Lambda treatment on immunologic parameters<br>Liver histology parameters |
| Study duration | Approximately 21 months (3 months for enrollment, 12 months of study treatment, 6 months of follow-up) |
| Study design | Randomized, open-label study of Lambda 120 or 180 μg subcutaneous (SC) injection weekly for 48 weeks in patients with chronic HDV infection. Patients will also take an anti-HBV nucleos(t)ide analog (NUC) from baseline (Day 1) through the end of the study. Clinic visits at baseline (Day 1), Weeks 1, 4, and every 4 weeks until Week 48. PD/efficacy of Lambda will be assessed by measuring HDV and HBV viral loads, viral serologies. Safety and tolerability of Lambda will be assessed by AE monitoring, clinical laboratory tests, physical examinations, vital signs, body weight, and concomitant medications. All enrolled patients will be followed for an additional 24 weeks off-treatment. All monthly follow-up visits will include evaluations of viral load (HDV and HBV), quantitative HbsAg (qHBsAg), anti all of the safety measures listed above. |
| Study population and number of patients | Twenty patients, 10 in each treatment group (120 or 180 μg daily) with chronic HDV infection with detectable HDV RNA by quantitative polymerase chain reaction (qPCR) will be enrolled.<br>Patients who discontinue the study before Week 12 for reasons other than an adverse event (AE) may be replaced on approval of the sponsor. |
| Eligibility criteria | Inclusion Criteria<br>Patients must meet all of the following inclusion criteria before study entry to be eligible for enrollment into the study:<br>1. Willing and able to comply with study procedures and provide written informed consent<br>2. Male or female, 18 to 65 years of age, inclusive<br>3. Chronic HDV infection of at least 6 months' duration documented by a positive HDV antibody (Ab) test, and detectable HDV RNA by qPCR at study entry |

TABLE 1-continued

4. Evidence of chronic hepatitis by liver biopsy within 6 months before screening. if liver biopsy is not available, the patient must be willing to consent to, and have no contraindication to, liver biopsy. Liver biopsy will be performed during screening.
5. Serum ALT > upper limit of normal (ULN) and <10 × ULN within 24 weeks prior to screening and at screening
6. Electrocardiogram (ECG) demonstrating no acute ischemia or clinically significant abnormality and a QT interval corrected for heart rate (QTcF) of >450 ms (males) or >450 ms (females)
7. Thyroid-stimulating hormone (TSH) and/or free T4 within 0.8 to 1.2 times the normal limit, or adequately controlled thyroid function as assessed by the investigator
8. For patients with diabetes, hypertension, or other risk factors for retinal disease, dilated retinal exam ≤1 year before screening by a licensed ocular specialist; for all other subjects, dilated retinal exam performed ≤1 year of screening documenting a normal eye exam per assessment of the investigator or a licensed ocular specialist
9. Female patients of childbearing potential and male patients with partners of childbearing potential must agree to use adequate methods of contraception during the study and for 1 month after end of study treatment. Adequate methods of contraception for patients or partner include the following:
   a) For females, two of the following contraceptive methods, with at least one being a barrier method
   b) Hormonal contraceptives for at least 3 months before the start of screening and for at least 90 days after last dose of study drug
   c) Intrauterine device (IUD) in place for at least 3 months before the start of screening and until 90 days after last dose of study drug.
   d) Double-barrier methods (use of condom [male partner] with either diaphragm with spermicide or cervical cap with spermicide) from the start of screening until 90 days after last dose of study drug.
   e) Surgical sterilization of the partner (vasectomy for 1 month before the start of screening and maintenance until at least 90 days after the last dose of study drug.
   f) For males
   g) Surgical sterilization (vasectomy for 1 month before the start of screening and maintenance throughout and for at least 90 days after the last dose of study drug).
   or
   h) Two effective forms of birth control from those listed below from the start of screening until 90 days after their last dose of study drug, with at least one being a barrier method:
   i) Consistently and correctly use a condom
   and
   j) Their partner must agree to use a hormonal contraceptive or a nonhormonal barrier method (IUD or diaphragm with spermicide or cervical cap with spermicide)
10. Willing and able to provide written informed consent
11. Willing and able to comply with all study procedures Exclusion Criteria
Patients meeting any of the following criteria will be excluded from the study:
General Exclusions
12. Participation in a clinical trial with or use of any investigational agent within 30 days before screening, or treatment with interferons or immunomodulators within 12 months before screening
13. Previous use of Lambda. Patients who previously participated in a clinical trial of Lambda but are confirmed to have received placebo or other non-Lambda interferons are allowed.
14. History or evidence of any intolerance or hypersensitivity to interferons or other substances contained in the study medication.
15. Female patients who are pregnant or breastfeeding. Male patients must confirm that their female sexual partners are not pregnant. Female patients must have a negative serum or urine pregnancy test (minimum sensitivity 25 IU/L or equivalent units of human chorionic gonadotropin [hCG]) within 24 hours prior to the start of investigational product.

Exclusions Based on Disease
16. Current or previous history of decompensated liver disease (Child-Pugh Class B or C)
17. Co-infected with human immunodeficiency virus (HIV) or hepatitis C virus (HCV). Positive results for HIV or HCV Ab at screening. Patients with a positive. HCV Ab at screening are allowed if they have completed a curative antiviral regimen and are documented to he HCV RNA negative (undetectable) at least 3 months before screening and at screening.
18. Past history or current evidence of decompensated liver disease or cirrhosis, defined as any of the following at screening:
   a. Bilirubin level ≥2.5 mg/dL unless due to Gilbert's disease
   b. Serum albumin level <3.5 g/dL
   c. International normalized ratio (INR) ≥1.5
   d. Alpha fetoprotein ≥100 ng/mL TABLE 1-continued 19. Evidence of significant portal hypertension such as hepatic venous pressure gradient (HVPG) ≥10 mmHg; current presence or history of variceal bleeding
20. Current evidence or history of ascites requiring diuretics or paracentesis, or hepatic encephalopathy
21. Any of the following abnormal laboratory test results at screening:
    a. Platelet count <90,000 cells/mm$^3$
    b. White blood cell (WBC) count <3,000 cells/mm$^3$
    c. Absolute neutrophil count (ANC) <1,500 cells/mm$^3$
    d. Hemoglobin <11 g/dL for women and <12 g/dL for men
    e. Serum creatinine concentration ≥1.5 × ULN
    f. Confirmed creatinine clearance (CrCl) <50 mL/min by Cockroft-Gault
22. Evidence of another form of viral hepatitis or another form of liver disease (eg, autoimmune liver disease, primary biliary cirrhosis, primary sclerosing cholangitis, Wilson's disease, alcoholic liver disease, nonalcoholic steatohepatitis, hemochromatosis, alpha-1-anti-trypsin deficiency)
23. History of hepatocellular carcinoma
24. Patients with any of the following:
    a. Current eating disorder or alcohol abuse
    b. Excessive alcohol intake, defined as follows: >20 g/day for females (1.5 standard alcohol drinks) or >30 g/day for males (2.0 standard alcohol drinks). A standard drink contains 14 g of alcohol: 360 mL of beer, 150 mL of wine, or 45 mL of spirits
    c. In the opinion of the investigator, an alcohol use pattern that will interfere with study conduct
    d. Drug abuse within the previous 6 months before screening, with the exception of cannabinoids and their derivatives
25. Prior history or current evidence of any of the following:
    a. Immunologically mediated disease (eg, rheumatoid arthritis, inflammatory bowel disease, severe psoriasis, systemic lupus erythematosus) that requires more than intermittent nonsteroidal anti-inflammatory medications for management or that requires use of systemic corticosteroids in the 6 months before screening (inhaled asthma medications are allowed)
    b. Retinal disorder or clinically relevant ophthalmic disorder
    c. Any malignancy within 5 years before screening. Exceptions are superficial dermatologic malignancies (eg, squamous cell or basal cell skin cancer treated with curative intent).
    d. Cardiomyopathy or significant ischemic cardiac or cerebrovascular disease (including history of angina, myocardial infarction, or interventional procedure for coronary artery disease)
    e. Chronic pulmonary disease (eg, chronic obstructive pulmonary disease) associated with functional impairment
    f. Pancreatitis
    g. Severe or uncontrolled psychiatric disorder, eg, depression, manic condition, psychosis, acute and/or chronic cognitive dysfunction, suicidal behavior, and relapse of substance abuse
    h. Active seizure disorder defined by either an untreated seizure disorder or continued seizure activity within the preceding year despite treatment with anti-seizure medication
    i. Bone marrow or solid organ transplantation
26. Other significant medical condition that may require intervention during the study. Patients with any serious condition that, in the opinion of the investigator, would preclude evaluation of response or make it unlikely that the contemplated course of therapy and follow-up could be completed. Patients for whom participation in the study would increase their risk.
Exclusions Based on Concurrent Medication Use
27. Therapy with an immunomodulatory agent; alpha interferon, either interferon alfa-2a or interferon alfa-2b, or pegylated interferon alfa-2a or alfa-2b; cytotoxic agent, or systemic corticosteroids within 12 months before screening
28. Use of telbivudine (Tyzeka or Sebivo) within 3 months before screening or during the study.
29. Current use of heparin or Coumadin
30. Received blood products within 30 days before study randomization
31. Use of hematologic growth factors within 30 days before study randomization
32. Systemic antibiotics, antifungals, or antivirals for treatment of active infection within 14 days before study randomization
33. Any prescription or herbal product the patient is taking, unless it is approved by the investigator
34. Long-term treatment (>2 weeks) with agents that have a high risk for nephrotoxicity or hepatotoxicity unless it is approved by the medical monitor
35. Medications or foods that are known moderate or strong inducers or inhibitors of cytochrome P450 (CYP)3A4 or CYP2C19. Moderate inducers or inhibitors of CYP2C19 can be used with caution if deemed necessary by the investigator TABLE 1-continued

| | |
|---|---|
| Test product, dose, and method of administration | 36. Drugs known to prolong the PR or QT interval<br>37. Receipt of systemic immunosuppressive therapy within 3 months before screening<br>Pegylated interferon lambda-1a (PEG-IFN-λ) (Lambda), 120 or 180 µg, weekly<br>SC administration |
| Duration of treatment | 48 weeks |
| Criteria for evaluation | The primary PD/efficacy endpoints are as follows:<br>  Proportion of patients with undetectable HDV RNA 12 weeks after EOT (SVR-12)<br>  Change from baseline in HDV viral load at Week 48 (EOT)<br>Additional PD/efficacy endpoints include:<br>  Proportion of patients with undetectable HDV RNA 12 weeks after EOT (SVR-24)<br>  Change from baseline in HDV viral load<br>  Change from baseline in HBV viral load<br>  Change from baseline in HBsAg levels<br>  Clearance of HBsAg<br>  Change from baseline in Fibroscan<br>  Liver biopsy improvement from baseline to Week 72 (EOFU)<br>Safety endpoints include:<br>  Treatment-emergent AEs and SAEs<br>  Treatment-emergent treatment-related AEs and SAEs<br>  AEs leading to early discontinuation of study treatment<br>  AEs leading to dose reduction<br>  Treatment-emergent changes in clinical laboratory findings<br>  Treatment-emergent changes in vital signs<br>  Treatment-emergent changes in ECG findings<br>  Treatment-emergent changes in physical examination results<br>  Usage of concomitant medications during the study |
| Statistical methods | The sample size of 20 will permit assessment of the safety, tolerability, and PD/efficacy of Lambda at 120 vs. 180 µg/week. The primary PD/efficacy endpoints will be assessed in the modified intention-to-treat (MITT) population, which will consist of all patients who receive at least 80% of the total study drug dose throughout the entire 48-week treatment period and for whom HDV viral load data are available for the Day 1 (baseline) and end-of-treatment (Week 48) study visits. |

At least one patient from the cohort of patients who receive at least 80% of the total study drug dose throughout the entire 48-week treatment period and for whom HDV viral load data are available for the Day 1 (baseline) and end-of-treatment (Week 48) study visits shows improvement in one or more endpoints as described in the protocol. In some embodiments, a patient exhibits a reduction in HDV viral load at end-of-treatment as compared to baseline. In some embodiments, a patient exhibits a reduction in HBV viral load at end-of-treatment as compared to baseline. In some embodiments, interferon lambda therapy reduces HDV viral substantially, such as to an undetectable level as measured 12 weeks after end-of-treatment. In some embodiments, a patient exhibits a reduction in the level of HBsAg at end-of-treatment as compared to baseline. In some embodiments, a patient exhibits improved clearance of HBsAg antigen.

Example 2. Treatment of HDV with Pegylated Interferon Lambda Monotherapy

In this study, patients with chronic HDV infection are randomly assigned treatment with either 120 mcg or 180 mcg pegylated interferon lambda 1-a as subcutaneous weekly injections for 48 weeks. To date, one enrolled patient has reached 8 weeks of treatment (patient 1). The change in the patient's HDV RNA levels from baseline through 8 weeks of treatment as a result of interferon lambda therapy is summarized in Table 2 below.

TABLE 2

| Visit | HDV RNA Quantitative (PCR) (IU/mL) |
|---|---|
| Baseline | 426 |
| Week 1 | 893 |
| Week 2 | 25 |
| Week 4 | 19 |
| Week 8 | <15 |

As shown in Table 2, following an initial increase in HDV RNA levels, the patient's HDV viral load decreased to a level below the Lower Limit of Quantification for the assay (<15 IU/mL).

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

What is claimed is:

1. A method of treating a hepatitis delta virus (HDV) infection in a human patient, the method comprising administering to the patient a therapeutically effective amount of interferon lambda for at least four weeks, wherein the patient is not co-infected with hepatitis C virus (HCV), and wherein the patient exhibits no evidence of an alternative liver disease selected from the group consisting of autoimmune liver disease, primary bilary cirrhosis, primary sclerosing cholangitis, Wilson's disease, alcoholic liver disease, nonalcoholic steatohepatitis, and hemochromatosis.

2. The method of claim 1, wherein the patient has compensated liver disease with or without cirrhosis.

3. The method of claim 2, wherein the patient has compensated liver disease with cirrhosis.

4. The method of claim 1, wherein the interferon lambda is pegylated.

5. The method of claim 4, wherein the interferon lambda is pegylated interferon lambda-1a.

6. The method of claim 1, wherein the interferon lambda is administered at a dose of 120 micrograms per week.

7. The method of claim 1, wherein the interferon lambda is administered at a dose of 180 micrograms per week.

8. The method of claim 1, wherein the interferon lambda is subcutaneously administered.

9. The method of claim 1, wherein the interferon lambda is administered for at least 6 months.

10. The method of claim 1, wherein the course of treatment results in an HDV viral load that is below 100 copies/mL serum or below 100 IU/mL serum.

11. The method of claim 10, wherein the HDV viral load remains below 100 copies/mL serum or below 100 IU/mL serum for at least 12 weeks after the end of treatment.

12. The method of claim 1, wherein the course of treatment results in an HDV viral load that is below the level of detection.

13. The method of claim 12, wherein the HDV viral load remains below the level of detection for at least 12 weeks after the end of treatment.

14. The method of claim 1, wherein prior to the onset of treatment, the patient has a serum alanine aminotransferase (ALT) level that is above the upper limit of normal (ULN), and the course of treatment results in an improvement in serum ALT level in the patient to a level that is within the ULN.

15. The method of claim 1, wherein the course of treatment results in a reduction in HBV viral load in the patient as compared to the patient's baseline HBV viral load at the initiation of treatment.

16. The method of claim 1, wherein the course of treatment results in improved liver function in the patient.

17. The method of claim 16, wherein the improved liver function is an improvement in one or more serum markers selected from the group consisting of serum albumin, bilirubin, alanine aminotransferase (ALT), aspartate aminotransferase (AST), prothrombin, alfa2-macroglobulin, apolipoproteinA1, haptoglobin, gamma-glutamyl transpeptidase (GGT).

18. The method of claim 16, wherein the improved liver function is an improvement in liver fibrosis.

19. The method of claim 1, wherein the method further comprises administering to the patient another antiviral or anti-HDV agent.

20. The method of claim 1, wherein interferon lambda is the sole or primary antiviral treatment or the sole or primary anti-HDV agent.

21. The method of claim 1, wherein the patient is not being treated with a CYP3A4 inhibitor.

22. The method of claim 1, wherein the course of treatment results in an HDV viral load that is undetectable.

23. The method of claim 1, wherein the course of treatment results in a reduction in HDV viral load in the patient of at least 1.5 log HDV RNA copies/mL compared to a baseline HDV viral load.

24. The method of claim 1, wherein the patient has a baseline HDV viral load of at least $10^2$ HDV RNA copies/mL serum at the initiation of treatment.

* * * * *

SEQUENCE LISTING

<160> NUMBER OF SEQ ID NOS: 1

<210> SEQ ID NO 1
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Asp Gly Asn Leu Ser Leu Arg Thr Ser Thr His Pro Glu Ser Thr
                165                 170                 175
```